US006246894B1

(12) United States Patent
Steuer et al.

(10) Patent No.: US 6,246,894 B1
(45) Date of Patent: Jun. 12, 2001

(54) SYSTEM AND METHOD FOR MEASURING BLOOD UREA NITROGEN, BLOOD OSMOLARITY, PLASMA FREE HEMOGLOBIN AND TISSUE WATER CONTENT

(75) Inventors: Robert R. Steuer, Pleasant View; David R. Miller, Morgan, both of UT (US)

(73) Assignee: In-Line Diagnostics Corporation, Riverdale, UT (US)

(*) Notice: Subject to any disclaimer, the term of this patent is extended or adjusted under 35 U.S.C. 154(b) by 0 days.

(21) Appl. No.: 09/028,809

(22) Filed: Feb. 24, 1998

Related U.S. Application Data

(63) Continuation-in-part of application No. 08/479,352, filed on Jun. 7, 1995, now Pat. No. 5,803,908, which is a continuation of application No. 08/317,726, filed on Oct. 4, 1994, now Pat. No. 5,499,627, which is a division of application No. 08/011,882, filed on Feb. 1, 1993, now Pat. No. 5,372,136, which is a continuation of application No. 08/598,169, filed on Feb. 7, 1996, now Pat. No. 5,734,502, which is a continuation of application No. 07/598,169, filed on Oct. 16, 1990, now abandoned.

(51) Int. Cl.$^7$ ............................................. A61B 5/00
(52) U.S. Cl. ............................................................ 600/322
(58) Field of Search .................................... 600/300, 310, 600/322–327

(56) References Cited

U.S. PATENT DOCUMENTS

| 5,101,825 | * | 4/1992 | Gravenstein | 600/326 |
| 5,372,136 | * | 12/1994 | Steuer et al. | 600/322 |
| 5,499,627 | * | 3/1996 | Steuer et al. | 600/322 |
| 5,692,503 | * | 12/1997 | Kuenstner | 600/322 |
| 5,836,132 | * | 11/1998 | Robinson | 600/310 |
| 5,857,462 | * | 1/1999 | Thomas et al. | 600/310 |
| 5,924,979 | * | 7/1999 | Swedlow et al. | 600/306 |

* cited by examiner

*Primary Examiner*—Robert L. Nasser
(74) *Attorney, Agent, or Firm*—Jacobson, Price, Holman & Stern, PLLC

(57) ABSTRACT

Systems and methods are provided for noninvasively measuring the levels of urea, blood osmolarity (or $Na^+$), plasma free hemoglobin and tissue water content in a patient's blood or tissue. Light of selected wavelengths is passed through blood or body tissue and the transmitted or reflected light is detected and the detected signals can be electronically compared and manipulated to provide the non-invasive, continuous and quantitative display of a patient's blood urea, blood osmolarity (or $Na^+$), plasma free hemoglobin and tissue water content.

8 Claims, 10 Drawing Sheets

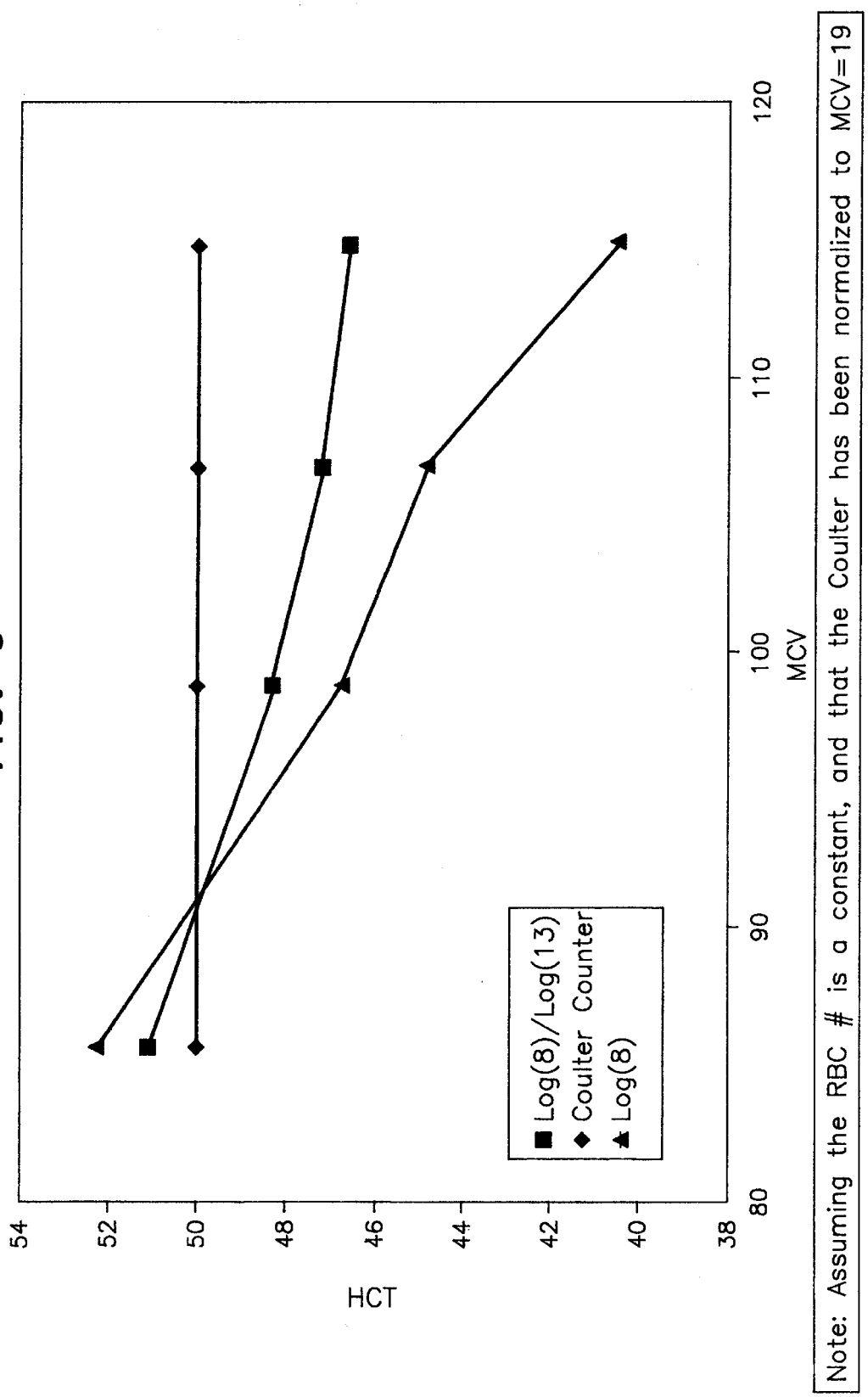

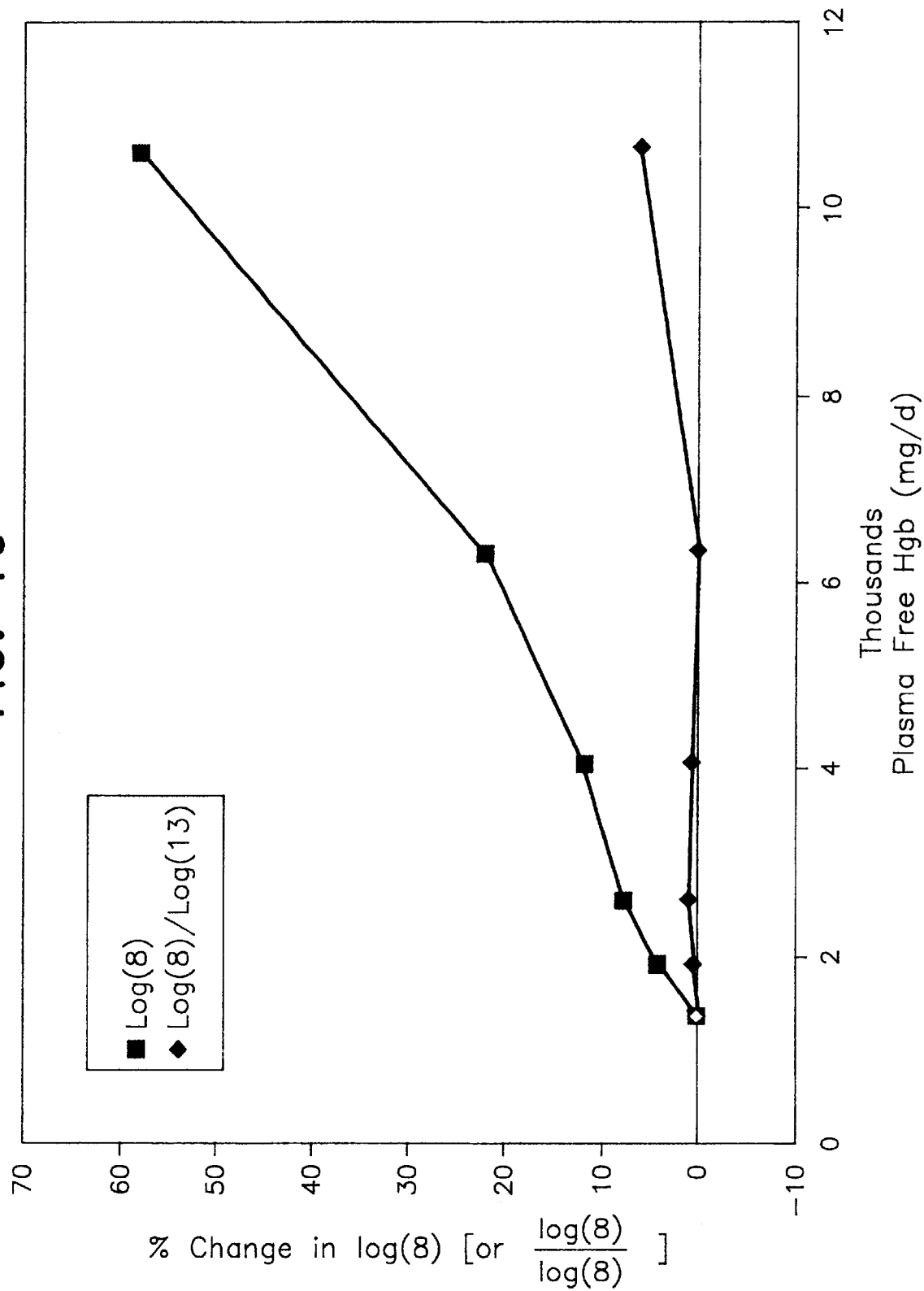

SYSTEM AND METHOD FOR MEASURING BLOOD UREA NITROGEN, BLOOD OSMOLARITY, PLASMA FREE HEMOGLOBIN AND TISSUE WATER CONTENT

RELATED U.S. APPLICATIONS

This is a Continuation-In-Part of Ser. No. 08/479,352, filed Jun. 7, 1995, now U.S. Pat. No. 5,803,908 which is a continuation of Ser. No. 08/317,726 filed Oct. 4, 1994, now U.S. Pat. No. 5,499,627, which is a divisional of Ser. No. 08/011,882 filed Feb. 1, 1993, now U.S. Pat. No. 5,372,136, which is a continuation of Ser. No. 08/598,169 filed Feb. 7, 1996, now U.S. Pat. No. 5,734,502, which is a Continuation of application Ser. No. 07/598,169 filed Oct. 16, 1990 now abandoned.

FIELD OF THE INVENTION

This invention relates to systems and methods for non-invasively and/or continuously and quantitatively measuring spectrophotometrically a patient's blood urea nitrogen, blood osmolarity, plasma free hemoglobin, and tissue water content.

BACKGROUND

Modern medical practice utilizes a number of procedures and indicators to assess a patient's condition. Blood urea nitrogen ("BUN"), plasma free hemoglobin ("PFH"), and tissue water content are important indications of a patient's condition.

BUN, which is the amount of urea or urea nitrogen per unit volume of blood expressed, typically, in milligram percent units (mg %) is typically a by-product of the catabolism of various body proteins principally found in muscle and liver tissues. It is present in extra (and intra) vascular spaces, but later processed and excreted through the kidneys into the urine. Specifically, in the case of end-stage renal disease patients, acute renal failure, or chronic renal failure, wherein the kidneys do not function properly to excrete this waste product, the BUN levels elevate. Subsequently, urea becomes a toxin to many other organ systems of the body including the brain, heart, skin, etc.

Medical professionals routinely desire to know the BUN, or dialysate urea or dialysate urea nitrogen (DUN) value, of the patient, because of the above-mentioned deleterious and serious side effects. To determine BUN using any of the techniques available today, it is necessary to draw a sample of blood by veni-puncture. Then, using widely accepted techniques, the sample of blood is subjected to biochemical and enzymatic reactions to determine the level of urea in the blood.

Conventional techniques require that a sample of blood be withdrawn from the patient for in-vitro analysis. Any invasion of the subject to obtain blood is accompanied by the problems of inconvenience, stress, and discomfort imposed upon the subject. The infectious risks are also present when the body is invaded, via needle-skin puncture. Additionally, withdrawing blood also creates certain contamination risks to paramedical professionals. Moreover, even in a setting where obtaining a blood sample does not impose any additional problems, for example during surgery, the available techniques require delay between the time that the sample is drawn and the BUN value is correctly processed. Still further, none of the previously available techniques allow for continuous monitoring of the subjects BUN as would be desirable during hemodialysis treatment procedures or even in intensive care treatment.

Specifically in hemodialysis, recent techniques have been developed to enzymatically determine the BUN level in the dialysate fluid as a marker of what is transpiring in the blood. However, these particular enzymatic techniques are likewise fraught with serious drawbacks, not the least of which is that the technique does not give a continuous measurement of the urea nitrogen even in the dialysate fluid. The enzymatic determination is accomplished by periodic, automated, sampling, wherein the enzymatic compounds and dialysate fluids are mixed and the urea nitrogen level is thereby determined.

Medical professionals routinely desire to know the tissue water (or hydration status) of the patient. For example, in hemodialysis (or in end-stage renal disease) patient tissue water increases dramatically due to the inadequate elimination of water from the interstitial and intravascular spaces, since the kidney no longer correctly functions. Hence, the patients become edematous and their tissue water content increases dramatically. In hemodialysis, the goal of therapy is to remove all of the toxins of the blood and body. Some of these toxins are the urea, potassium, and even water which can become a significant toxin to the patient. Therefore, removal of water from the tissue is crucial because this water overloaded state requires excessive energy expenditure by the heart to function. Hence, many dialysis patients are in a state of pulmonary edema, congestive heart failure, etc., due to the large "load" that the heart must push against. Therefore, to reach an appropriate "dry weight" (the patient's body weight when the kidneys were functioning normally) is an important dialysis therapy goal.

Medical professionals in other specialties are desirous of knowing the tissue water content of non-renal, edematous patients for other reasons. Hormonal imbalances, menstrual cycle variations, congestive heart failure and other causes also result in pulmonary edema and peripheral edema. These states require the knowledge of the interstitial tissue water content.

Tissue water content is conventionally measured by bio-electrical impedance; however, bioimpedance can be costly and requires the injection of small electrical currents into the patient. Another technique involves measuring the amount of water in the tissue spaces by injecting radio-isotopes into a patient. This is done principally on a research basis, however, because of the attendant radiation risks.

PFH (Plasma Free Hemoglobin) is the amount of hemoglobin not contained inside a red blood cell, but rather free in plasma solution and is expressed, typically in milligram percent units (mg %). PFH is typically a result of red blood cell breakage or hemolysis, with spillage of the hemoglobin directly into the plasma. Specifically, in the case of end-stage renal disease patients, acute renal failure, or chronic renal failure, wherein the kidneys do not function properly and hemodialysis is required, the PFH levels in the blood may elevate due to tubing lines kinking and pump rollers crushing the red blood cells during the course of the hemodialysis treatment. This can occur in cardio-pulmonary surgeries as well. Subsequently, PFH itself becomes a toxin to many other organ systems of the body.

Medical professionals desire to know the PFH of the patient, because of the above mentioned deleterious and serious side effects associated with the presence of PFH. In conventional techniques, PFH is measured by drawing a sample of blood by veni-puncture. Then, using widely accepted techniques the sample of blood is subjected to biochemical reactions to determine the level of PFH in the plasma of the blood.

Blood osmolarity is the osmolar content of blood per unit volume of blood expressed, typically, in milliosmolar units. The osmolar content of blood (and/or the sodium content) should have a narrow range of values due to the body's compensatory abilities. However, in the case of end-stage renal disease patients, acute failure, or chronic renal failure, wherein the kidneys do not function properly and hemodialysis is required, the blood osmolarity varies greatly.

Medical professionals routinely desire to know the osmolarity or sodium value of the patient, because of the deleterious and serious side effects associated with levels outside the normal range. To determine the blood osmolarity (OSM) or blood sodium ($Na^+$) content using any of the techniques available today, it is necessary to draw a sample of blood by veni-puncture. Then, using widely accepted techniques the sample of blood is subjected to physical and biochemical reactions to determine the level of OSM or $Na^+$ in the blood.

In view of the drawbacks in the available art dealing with invasive blood constituent determinations, it would be an advance in the art to noninvasively and quantitatively determine a subject's blood constituent including BUN, PFH, tissue water, osmolarity, and $Na^+$. It would also be an advance to provide a system and method for noninvasive blood constituent monitoring which utilizes electromagnetic emissions as the information carrier for information relating to BUN, PFH, tissue water, osmolarity, and $Na^+$.

OBJECTS OF THE INVENTION

It is an object of the present invention to provide a method and system for noninvasively measuring and monitoring tissue water.

It is another object of the present invention to provide a method and system for noninvasively measuring and monitoring urea in the blood or dialysate fluid.

It is a further object of the present invention to provide a method and system for noninvasively measuring and monitoring PFH in the blood.

It is yet an object of the present invention to provide a method and system for noninvasively measuring and monitoring osmolarity and $Na^+$ of the blood.

SUMMARY OF THE INVENTION

In general, the present invention is directed to apparatus and methods for determining a biologic constituent value, such as BUN, PFH, tissue water and osmolarity, transcutaneously, continuously, and noninvasively.

One aspect of the present invention provides a method and system for the noninvasive measurement of tissue water content in which an emitter and a detector are positioned outside of a patient (either remote from the patient or, preferably, mounted on the skin of a patient), light from the emitter passes through a portion of a patient's body and is received by the detector. The detector measures light of a selected wavelength that is absorbed by water. The intensity of light at an initial time is measured by a detector; then at a later time, typically after a period of dialysis, the intensity of detected light is compared with the initial intensity and the percent change in tissue water is calculated.

In an alternate method, light of at least two selected wavelengths are detected and absorptions due to blood and/or skin tissues are accounted for. Thus a measurement of intensity transmitted (i.e. detected) versus intensity emitted at a wavelength selected for absorption by water allows calculation of the volume percent of water in a patient's tissue.

Another aspect of the present invention also provides a method and system for the measurement of urea concentration in the blood of a patient by measuring the quantities of light at two wavelengths where the function of the extinction coefficient versus urea concentration at each given wavelength holds BUN information that is different in at least one of curvature, offset, linearity or sign from the other wavelength.

A further aspect of the present invention provides a method and system for measuring osmolarity (or sodium content) of a patient's blood.

Yet another aspect of the present invention provides a method and system for measuring plasma free hemoglobin through an optical technique.

BRIEF DESCRIPTION OF THE DRAWINGS

FIG. 9 shows plots of hematocrit (HCT) as measured by three techniques vs. mean cell volume (MCV).

FIG. 10 shows plots of the % change in absorbance of light at 810 nm and 810 nm/1300 nm vs. PFH.

DETAILED DESCRIPTION OF THE INVENTION

Figure 2:
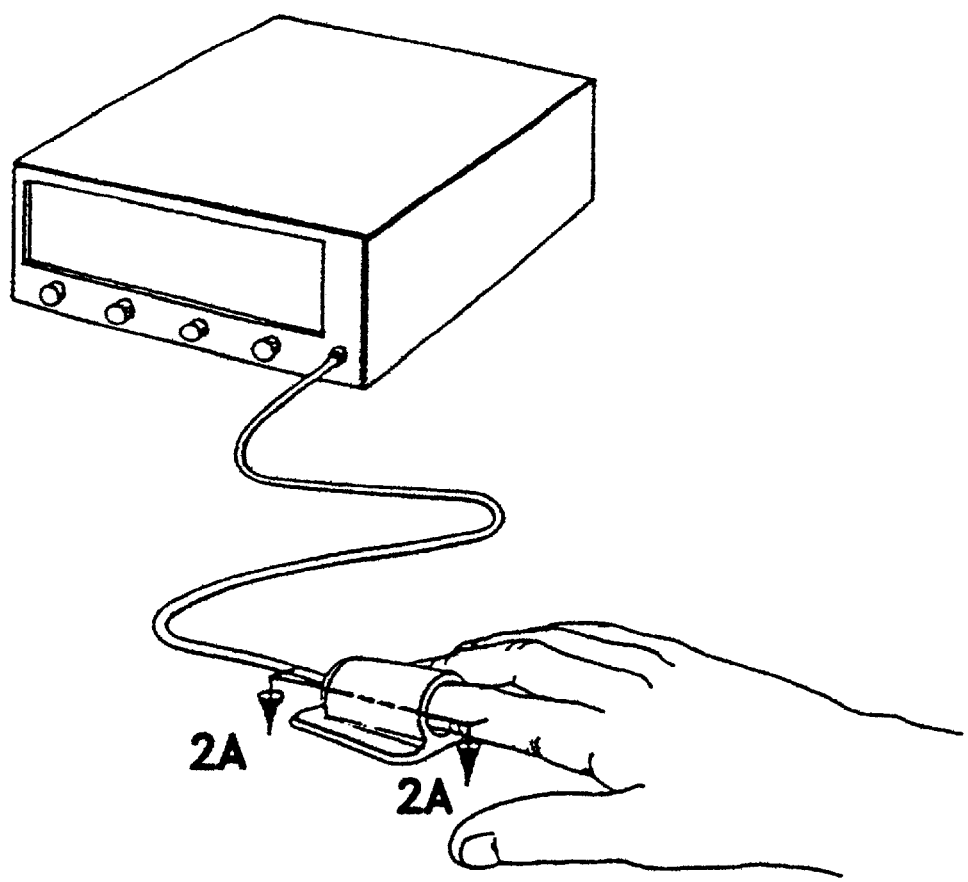
FIG. 2 shows a perspective view of apparatus used to noninvasively measure tissue water content.
Figure 2A:
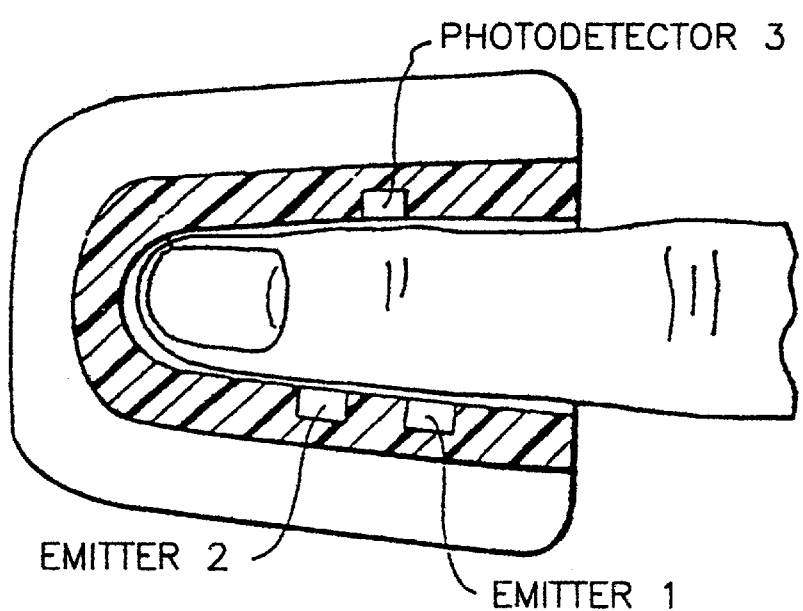
FIG. 2A shows an enlarged cross-sectional view of a patient's finger in the apparatus of FIG. 2, configured in a transmission mode.
Figure 3:
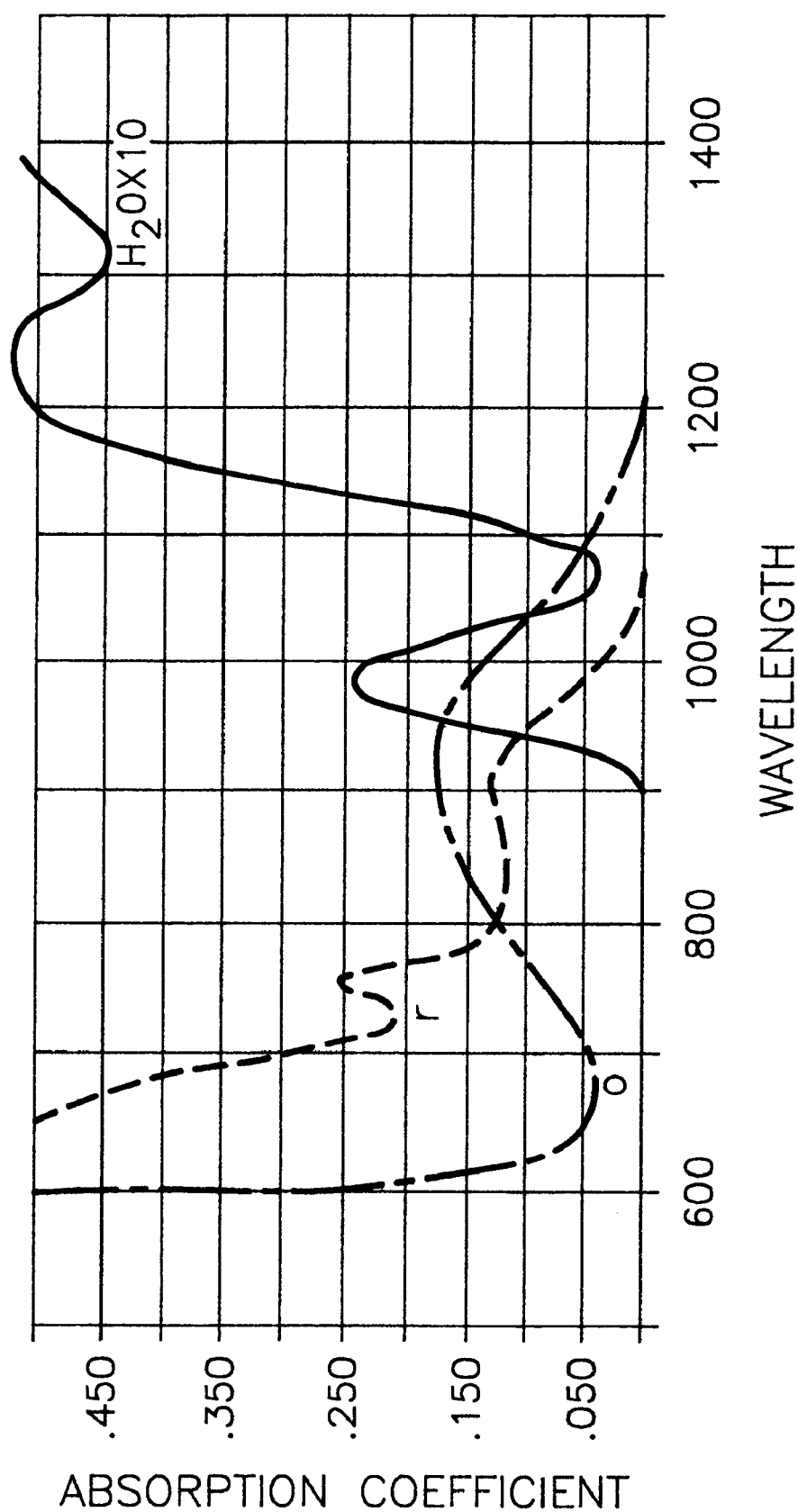
FIG. 3 shows absorption coefficient values for oxyhemoglobin, reduced hemoglobin and water.
Figure 4:
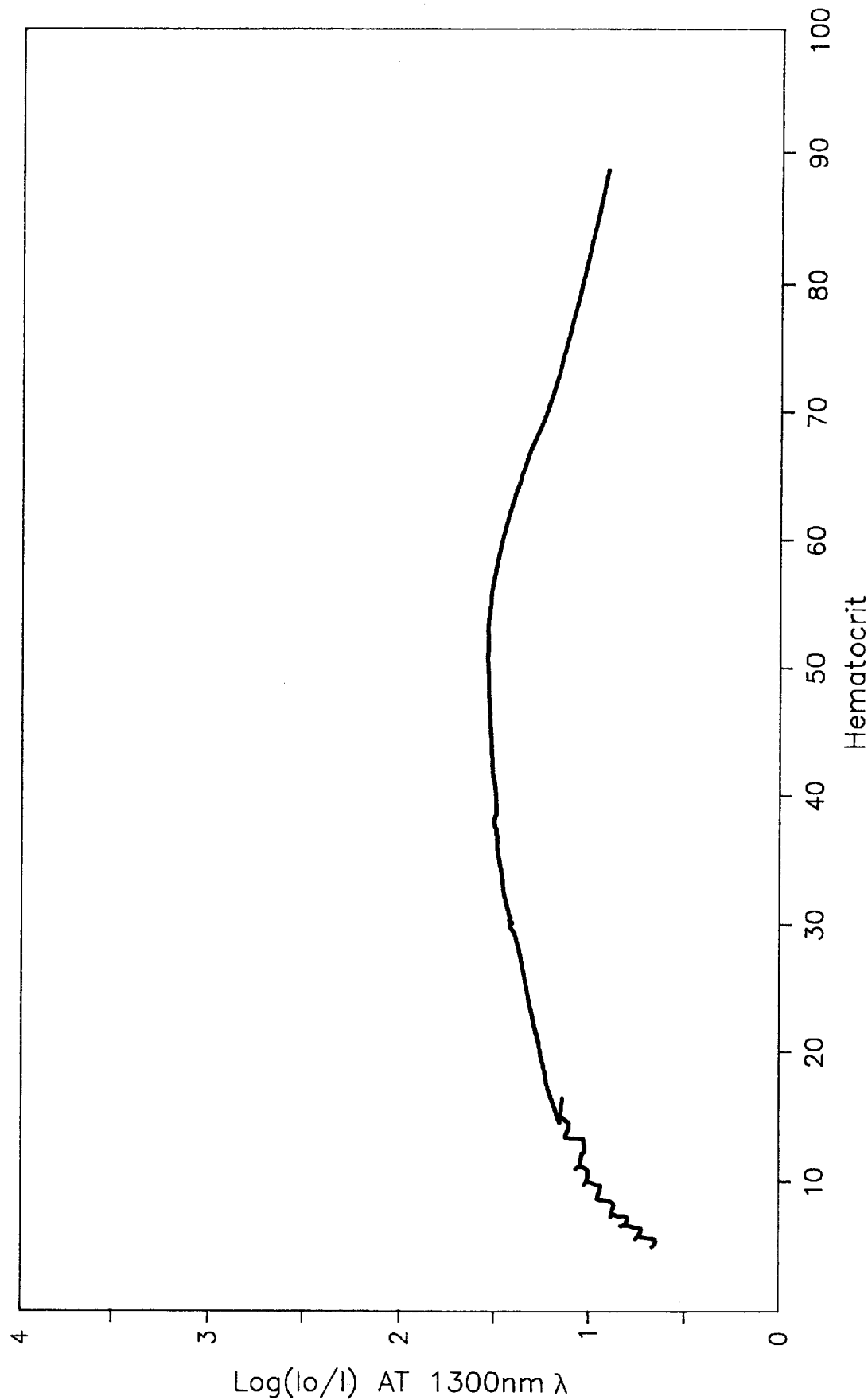
FIG. 4 shows a plot of Log (Io/I) at 1300 nm wavelength versus hematocrit of a blood sample as it is diluted with saline to show that intensity of light has slight dependence on Hematocrit.

In general, the present invention is directed to apparatus and methods for determining a biologic constituent value transcutaneously, continuously, and noninvasively. This is achieved by passing at least one wavelength of light onto or through body tissues such as the finger, earlobe, or scalp, etc., see FIG. 2 and 2A, and then compensating for the effects of the other non-water, body tissues using a modified Beer Lambert Law as a theoretical basis. An example of such a measurement technique is found in U.S. Pat. No. 5,372,136 and is incorporated herein.

Although the present invention will describe in great detail the transillumination of blood in an extracorporeal conduit, it will be appreciated that reflectance spectrophotometry may alternatively be employed when transillumination is difficult to accomplish. As used herein, the term "body part" is intended to include skin, earlobe, fingertip, lip, etc., but also "extracorporeal conduit", see FIG. 1, may refer to a disposable blood chamber or in-vitro blood containers such as tubes and cuvettes.

In preferred embodiments, measurements are conducted using the apparatus (or modified versions thereof) described in U.S. Pat. Nos. 5,456,253 (column 1, line 18 through column 14, line 67; FIGS. 1–13) and 5,372,136 (column 1, line 12 through column 14, line 39; FIGS. 1–16), and U.S. patent application Ser. No. 08/479,352 which are incorporated herein as if reproduced in full below.

By way of background, kidneys are located on either side of the spine. In a healthy patient, kidneys function to stimulate red blood cell production and regulate the content of the blood. Kidneys also produce hormones that affect other organs and control growth. When functioning properly, kidneys serve as a means for cleaning the blood by removing excess fluids and toxins. The filtering task in each kidney is performed in part by the some one million nephrons in the kidney. The nephrons are filtering units made up of tiny blood vessels. Each such blood vessel is called a glomerulus. Every day, roughly 200 quarts of blood and fluids will be processed by the kidney. The kidney removes about two quarts of water and toxic chemicals which are sent to the bladder as urine for subsequent voiding thereof by urination.

Figure 1:
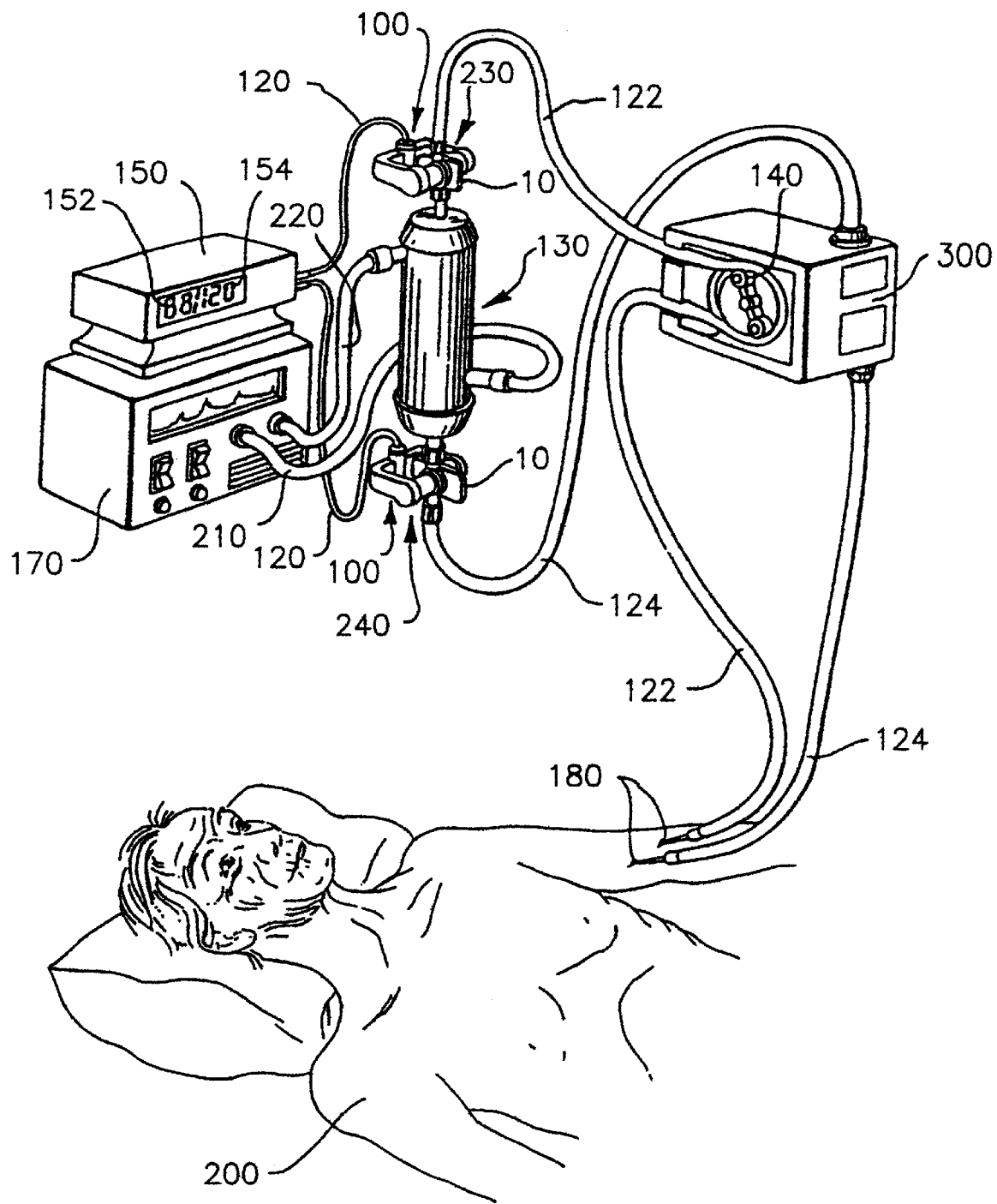
FIG. 1 shows a typical hemodialysis tubing circuit and connections.

A patient whose kidneys are performing substandardly may be dialyzed as a substitute for the blood cleansing function normally performed by property functioning kidneys. Dialysis is a process by which the function of the kidney of cleaning blood is substitutionarily performed. The process of dialysis was perfected for routine use in the 1960's, having been invented some 50 years ago. For the purposes of discussion and illustration of hemodialysis, FIG. 1 is now referred to. While FIG. 1 incorporates a view of a presently preferred embodiment of the present invention, it also incorporates a view of some common components which are typical in a general hemodialysis environment. The general environment of hemodialysis and typical components therein will now be discussed.

In hemodialysis, blood is taken out of a patient 200 by an intake catheter means, one example of which is shown in FIG. 1 as an input catheter 122. Input catheter 122 is intravenously inserted into patient 200 at a site 180 and is used for defining a blood passageway upstream of a blood filter used to filter the impurities out of the blood. The blood filter is also called a dialyzer 130. The unclean blood flows from an artery in patient 200 to a pump means, an example of which is pump 140. From pump 140, the blood flows to dialyzer 130. Dialyzer 130 has an input port 230 and an output port 240. The pump 140 performs the function of moving the unclean blood from patient 200 into input port 230 through dialyzer 130, and out of dialyzer 130 at output port 240.

Specifically, unclean blood in input catheter 122 is transported to input port 230 of dialyzer 130. After passing through and being cleansed by dialyzer 130, the blood may receive further processing, such a heparin drip, in hemodialysis related component 300. The now clean blood is returned to patient 200 after the dialyzing process by means of an output catheter means, an example of which is output catheter 124. Output catheter 124, which is also intravenously inserted into patient 200 at site 180, defines a blood passageway which is downstream from dialyzer 130, taking the blood output by dialyzer 130 back to patient 200.

As mentioned, the hemodialysis process uses a blood filter or dialyzer 130 to clean the blood of patient 200. As blood passes through dialyzer 130, it travels in straw-like tubes (not shown) within dialyzer 130 which serve as membrane passageways for the unclean blood. The straw-like tubes remove poisons and excess fluids through a process of diffusion. An example of excess fluid in unclean blood is water and an example of poisons in unclean blood are blood urea nitrogen (BUN) and potassium.

The excess fluids and poisons are removed by a clean dialysate liquid fluid, which is a solution of chemicals and water. Clean dialysate enters dialyzer 130 at an input tube 210 from a combined controller and tank 170. The dialysate surrounds the straw-like tubes in dialyzer 130 as the dialysate flows down through dialyzer 130. The clean dialysate picks up the excess fluids and poisons passing through the straw-like tubes, by diffusion, and then returns the excess fluids and poisons with the dialysate out of dialyzer 130 via an output tube 220, thus cleansing the blood. Dialysate exiting at output tube 220 after cleansing the blood may be discarded.

The general hemodialysis process and environment is seen in FIG. 1 and has been described above. A summary of this process is that patient 200, whose kidneys are performing substandardly, is dialyzed. The unclean blood flows from an artery in patient 200 to the pump 140 and then to dialyzer 130. Unclean blood flows into dialyzer 130 from input catheter 122, and then clean blood flows out of dialyzer 130 via output catheter 124 back to patient 200.

It is preferable that the pump 140 causes the blood flowing into, through, and out of dialyzer 130 to flow in a pulsatile fashion.

Installed at either end of dialyzer 130 is a spectrophotometry means for defining a blood flow path, for emitting radiation into the blood in the flow path, and for detecting radiation passing through both the blood and the flow path. The spectrophotometry means includes a cuvette means 10 for defining the blood flow path, and an emitter/detector means 100 for directing and detecting radiation. Within the emitter/detector means is both an emission means for directing radiation and a detector means for detecting radiation. Once such spectrophotometry means is discussed in detail in U.S. Pat. No. 5,456,253 and is incorporated by reference herein.

Emitter/detector apparatus 100 enables the detection by a photodetector (not shown) of the portion of radiation which is directed by a photoemitter (not shown) to cuvette 10 and passes through both the blood therein and the cuvette 10. As shown in FIG. 1, the cuvette 10 is installed at either end of dialyzer 130. Each cuvette 10 has a photoemitter and a photodetector thereon.

The emitter/detector means is electrically connected to a calculation means. In a preferred embodiment of the system, an example of the calculator means is depicted in FIG. 1 as computer 150 which is electrically connected to the photoemitter and the photodetector on emitter/detector apparatus 100 by means of cable 120.

Intake catheter 122 takes blood to cuvette 10 situated before input port 230 of dialyzer 130. Emitter/detector apparatus 100 at input port 230 of dialyzer 130 subjects the blood therein to at least two radiation wavelengths of electromagnetic radiation for the purposes of analysis, via spectrophotometry, so that the concentration of a desired biological constituent can be derived. Each photodetector, at both input port 230 and output port 240 of the dialyzer 130, communicates the detected radiation at least a first and a second wavelength via cable 120 to computer 150.

Computer 150 calculates both before dialysis and after dialysis concentrations of the sought-after or desired biological constituent. Computer 150 then displays, respectively, at a first display 152 and a second display 154, the derived concentration of the biological constituent in their analogue or digital representations.

It should be understood that the improvements and modifications of the present invention can be applied to a wide variety of blood monitoring apparati and, thus, are not limited to certain preferred embodiments such as those described in the above-cited U.S. patents.

The theoretical basis for the spectrophotometric technique mentioned above is the Beer Lambert Law as shown below.

$$I = I_o e^{-E(x)d} \tag{1}$$

Wherein $I_o$ is the intensity of the incident source radiation, I is the transmitted intensity of the source radiation through the sample, E is the extinction coefficient of the sought for constituent, x is the concentration of the sample constituent in the tissue (or blood conduit), and d is the optical path length (distance).

Utilizing the Beer-Lambert Law, quantitative measurements have not been possible in the body or whole blood since the scattering of the incident photons passing into and through the measuring container (or skin) regions is extensive and highly variable. This scattering spoils the Beer-Lambert Law by adding a variable loss of radiation to the measurement and also extends the path length of the incident radiation by an unknown amount as well. Therefore modifications to the Beer-Lambert Law are required and will be hereafter shown.

Since it is important to know when the patient's interstitial water has been completely removed from the tissue or that the patient's "dry weight" has been achieved, the following equations describe the methodology by which a value or graphic representation, digital or analog, can be determined. A modified Beer Law equation for tissue can be approximated as:

$$I \approx I_o e^{-[(3K(K+S))^{1/2}]d} \tag{2}$$

When K and S are the bulk absorbance and scattering coefficients of tissue. For human tissue K is <<S and hence for small changes in tissue absorption a more accurate expression is:

$$I = I_o \cdot \frac{\alpha}{S \cdot d^2} \cdot e^{-\alpha \cdot d}, \text{ where } \alpha = (3KS)^{1/2} \tag{3}$$

Since S, the scattering term, is relatively constant for a given tissue, the absorbance term, K, takes the form:

$$K = K_b X_b + K_w X_w + K_s X_s \tag{4}$$

Where:
$K_b$=absorbance due to blood
$K_w$=absorbance due to water
$K_s$=absorbance due to skin tissues
$X_b$=volume of blood per volume of tissue
$X_w$=volume of water per volume of tissue and
$X_s$=volume of skin per volume of tissue.

MEASURING TISSUE WATER

In hemodialysis usage, the tissue water content is most important, since the clinician is attempting to measure the tissue hydration status after which no further water can be removed. Hence measuring the optical power at about 1300 nm from the start (initial, $(I_1)_{13}$) of hemodialysis to some time (t) is given from equation 3 measured at separate d's, $d_1$ and $d_2$; and where $I_{01} = I_{02}$:

$$\log\left(\frac{I_1 d_1^2}{I_2 d_2^2}\right)_i = -[(3K_i S_i)^{1/2}] \cdot d\Delta \tag{5}$$

and $$\log\left(\frac{I_1 d_1^2}{I_2 d_2^2}\right)_t = -[(3K_t S_t)^{1/2}] \cdot \Delta d \tag{6}$$

To determine the % change in $X_w$, % $\Delta X_w$, the following obtains:

$$\left\{\log\left(\frac{I_1 d_1^2}{I_2 d_2^2}\right)_i \Big/ \log\left(\frac{I_1 d_1^2}{I_2 d_2^2}\right)_t\right\} = \gamma = (K_i S_i / K_t S_t)^{1/2} \tag{7}$$

Again, since $S_i \approx S_t$ and substituting equation 4 into equation 7, the following obtains:

$$\gamma = [(K_b X_b + K_w X_w + K_s X_s)_i / (K_b X_b + K_w X_w + K_s X_s)_t]^{1/2} \tag{8}$$

But at a wavelength of about 1300 nm, $K_b$ and $K_s$ are about equal to $K_w$, hence:

$$\gamma^2 = \frac{K_w \cdot (1 + X_b / X_{wi} + X_s / X_{wi}) \cdot X_{wi}}{K_w \cdot (1 + X_b / X_{wt} + X_s / X_{wt}) \cdot X_{wt}} \tag{9}$$

and hence:

$$\gamma^2 \approx X_{wi} / X_{wt} \tag{10}$$

Therefore the percentage change in tissue water ($X_w$) becomes:

$$[\gamma^2 - 1] \times 100 = [(X_{wi} / X_{wt}) - 1] \times 100 \tag{11}$$

As mentioned above, for the determination of the tissue water content in patients with congestive heart failure, etc., the absolute value of the tissue water may be desired. Hence, the following indicate the mathematical operations required to determine the absolute value of tissue water, see FIG. 6. The following operations indicate the need for additional wavelengths in order to eliminate or compensate for the scattering effects of other competing biologic constituents in tissue. From equations 3, 4, 5 and 6 knowing $\Delta d$, it is necessary to measure S exactly (or eliminate S) to calculate $X_w$ directly. S has been measured previously and found to be 0.75/mm, and relatively constant for human tissue. There may be a need to collect data from additional wavelengths in order to eliminate or compensate for the scattering effects of other competing biologic constituents in tissue.

In summary, one aspect of the present invention is directed to apparatus and methods for determining the biologic constituent value, the tissue water value, transcutaneously and noninvasively. This is achieved by passing at least one wavelength of light onto or through body tissues such as the finger, earlobe, scalp, etc. and then compensating for the effects of other body tissues not related to water. The light can also be passed directly through blood in a conduit. In one embodiment within the scope of the present invention, the wavelength of light is selected to be near 1300 nanometers (nm). At that particular wavelength, blood is almost independent of the hematocrit value but the water absorption coefficient at 1300 nm is very large compared to that of blood. Hence, the measurement at 1300 nm is independent of the hemoglobin content of the tissue per se. Another significant advantage of the present invention is the capability of monitoring multiple wavelengths simultaneously other than 1300 nm, where water absorption is even greater than that at 1300 run. However, at those wavelengths (1480 nm, 1550 nm, 1800 nm and 1900 nm) the simultaneous compensation for the hemoglobin value is required.

DETERMINING BLOOD UREA NITROGEN

A modified Beer-Lambert equation can also utilized for the determination of urea in the blood as follows:

$$I = I_o e^{[-E(x)d + B(d, E(x))]} \quad (12)$$

where B (d,Ex)) is an optical pathlengthening function, Io is the intensity of the incident source radiation, I is the transmitted intensity of the source radiation through the sample, E is the extinction coefficient of the sought for constituent, x is the concentration of the sample constituent in the tissue (or disposable blood conduit) and d is the optical separation distance.

Figure 5:
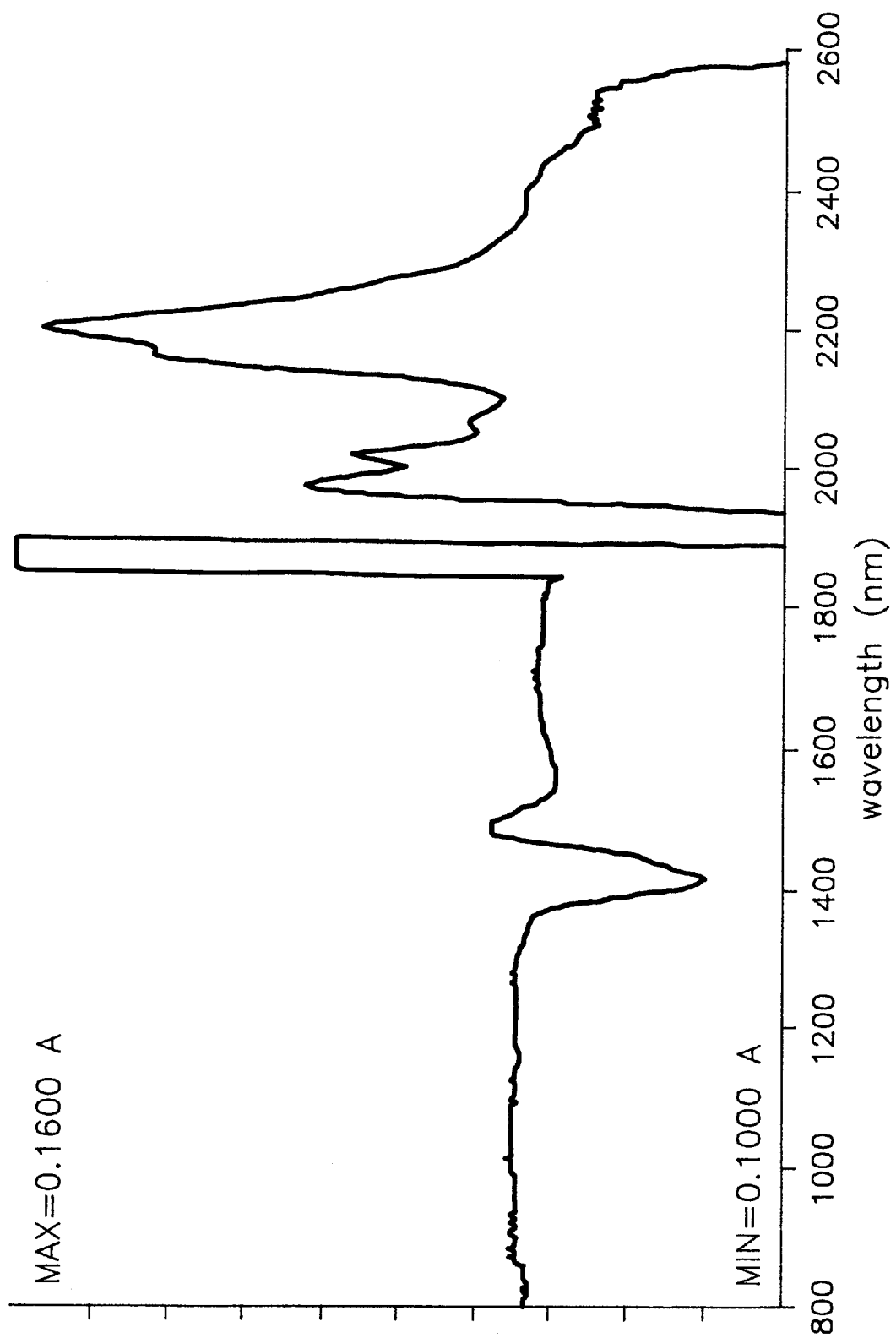
FIG. 5 shows an absorption spectrum of 14% urea at room temperature.

To determine BUN according to the present invention, a measuring wavelength (M) and a reference wavelength (R) must be selected. These wavelengths may be selected close enough to one another such that the pathlengthening factors are approximately the same for each wavelength (longer wavelengths are preferred since they exhibit less sensitivity to scattering). For example, the selection of a measuring wavelength at 2190 nm and a reference wavelength at 1900 nm may be appropriate since the scattering functions (pathlengthening factors) are approximately the same at these wavelengths, and the difference between the peak BUN absorption at 2190 nm and the minimal urea absorption at 1900 nm holds significant BUN information, as seen in FIG. 5.

Figure 6:
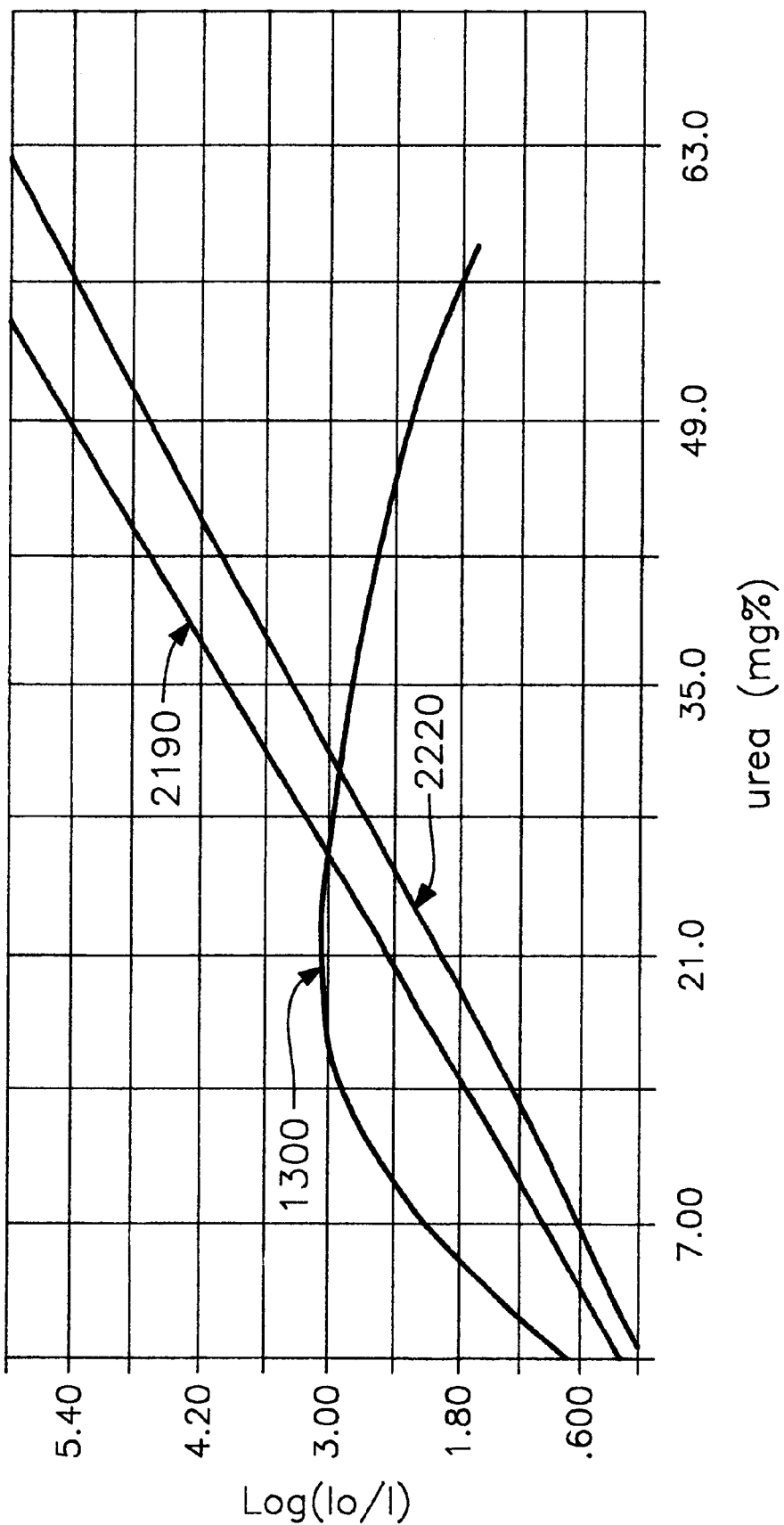
FIG. 6 represents a hypothetical plot of log light intensity vs. urea concentration (milligram percentage, mg %).

The actual function of extinction coefficient E (either $E_M$ or $E_R$) versus the urea concentration at each given wavelength must hold BUN information that is different in at least one of curvature, offset, linearity, or sign from the other wavelength, see the hypothetical curves in FIG. 6. If the functions of E versus urea concentration are not sufficiently different for each wavelength, then the ratio $E_M/E_R$ will not hold BUN information. Even though wavelengths of 2190 nm and 1300 nm are the preferred wavelengths (see FIG. 5), it will be appreciated that other wavelengths such as 2200 nm (2980 nm or 6160 nm) and 1480 nm (or 1900 nm) may also satisfy the condition of having adequate urea detected with respect to water.

For monitoring the BUN in living tissue of a patient, the pulsatile characteristics of the blood require the utilization of the form and mathematical operations presented in U.S. Pat. No. 5,372,136, and using the described ΔI/I technique in order to eliminate certain intrinsic tissue and extrinsic light source effects.

In non-pulsatile applications such as hemodialysis or where blood or dialysate is flowing through a chamber or cuvette, logarithmic operations will give the appropriate computed BUN values, as shown in the following formulation for the two example wavelengths:

$$[BUN]_{raw} = log\ (I/I_o)_{2190}/log\ (I/I_o)_{1300} = E_{2190}/E_{1300} \quad (13)$$

But since the whole blood medium will have some hematocrit dependence at 2190 nm, use of the following formula compensates for the hematocrit effects:

$$[BUN]_{corrected} = [E_{2190}/E_{1300}] \cdot [F\ [log\ (I/I_o)_8/log\ (I/I_o)_{13}]] \quad (14)$$

where $F[(log_8/log_{13})]$ is a function of the hematocrit. It is likely that other competing substances will be detected at 2190 nm, those can also be compensated with similar functional operators.

In a preferred embodiment, the electronic structure and memory components for a BUN measuring system are similar to that described in U.S. Pat. No. 5,372,136. In some preferred embodiments, the wavelengths 1300 nm, 1800 nm, 1900 nm, and 2190 nm are selected. Telcom Device Corp. of Camarillo, Calif. manufactures the corresponding LEDs with product numbers: 1300 nm LED, 1.8 LED, 1.9 LED and 2.2 LED. A preferred source for the detector may be photodiode, PD24-04, manufactured by IBSG, St. Petersburg, Russia. Although the foregoing discussion relates to noninvasive analysis of BUN (or dialysate urea nitrogen, DUN) information in the hemodialysis setting, it will be appreciated that emitters, sensors, and circuitry can be adapted for invasive, in-vitro analysis of BUN, or the transcutaneous, in-vivo analysis.

To summarize, one embodiment of the present invention that measures BUN, one wavelength of light is selected to be at or near the peak absorption level of urea and another wavelength (the reference) selected at an absorption minimum of urea (or urea nitrogen) with respect to water. One such peak wavelength for urea (or urea nitrogen) is at 2190 nanometers (nm) and one such reference wavelength with respect to water may be 1300 nm wavelength of light. Other wavelengths of significant absorption due to water (the reference) and minimal absorption due to urea or urea nitrogen are also present at 1480 nm, 1550 nm, 1800 nm, 1900 nm, etc.

In the presence of blood however, at 2190 nm, hemoglobin (or hematocrit) absorption (and scattering) also exists, therefore one must compensate the 2190 nm absorption value with the hematocrit (or hemoglobin) value. However, at the 1300 nm wavelength, the absorbency due to hematocrit or hemoglobin is minimal.

MEASURING OSMOLARITY AND SODIUM CONTENT

Figure 7:
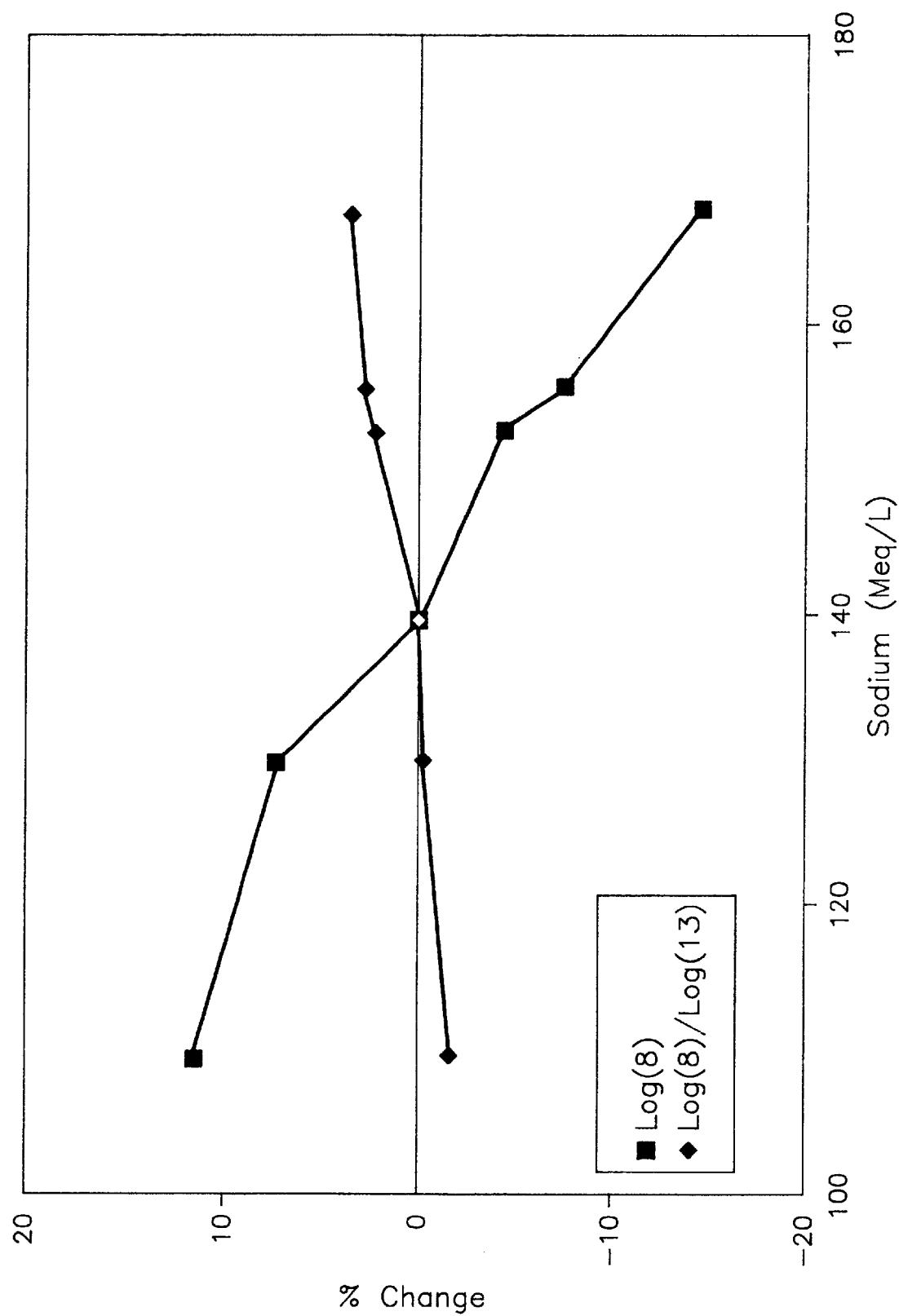
FIG. 7 shows plots of the % change in absorbance of a beam of light at 810 nm and 810 nm/1300 nm v. sodium.
Figure 8:
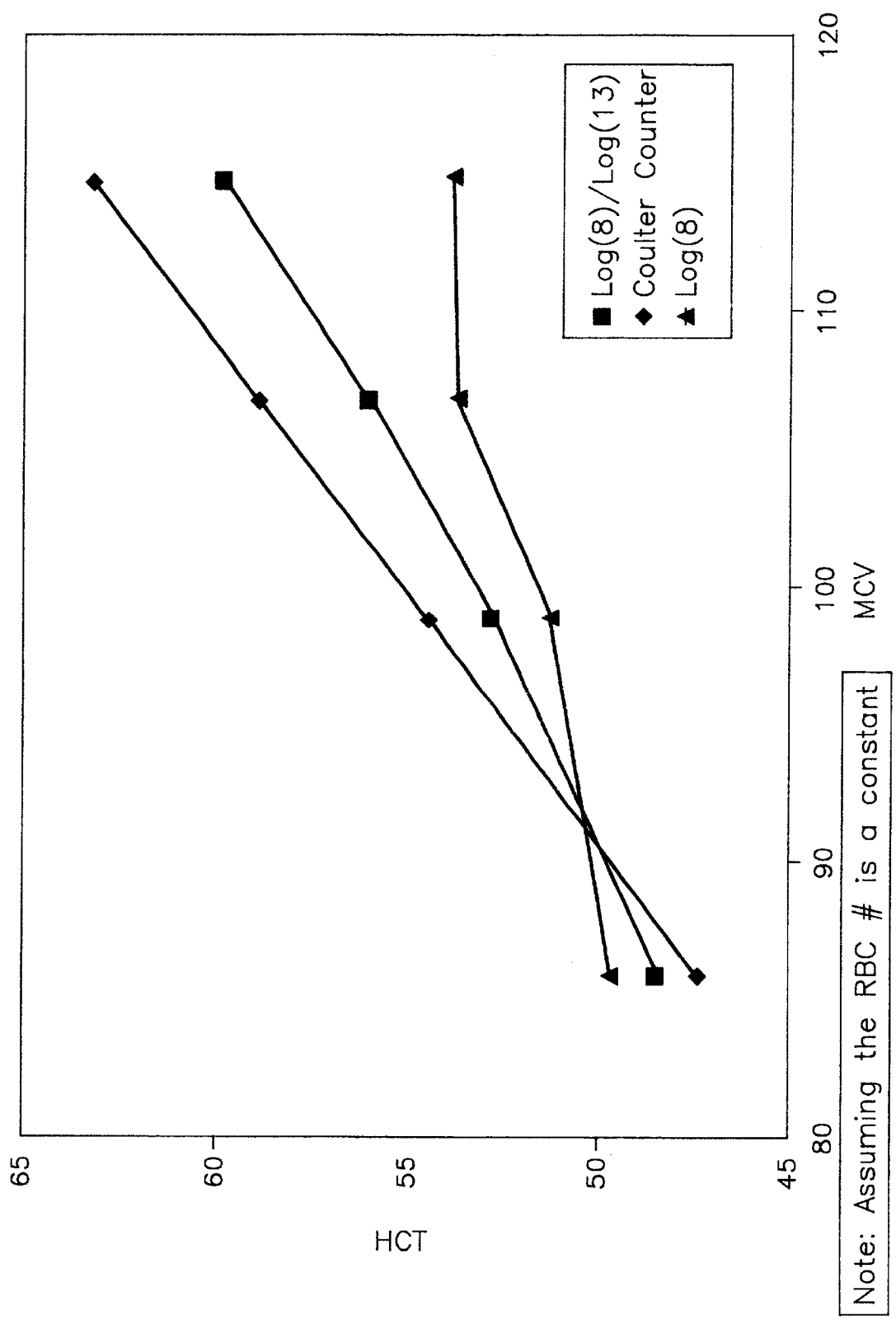
FIG. 8 shows plots of hematocrit (HCT) as measured by three techniques vs. mean cell volume (MCV).

The functional relationships between $Na^+$ and osmolarity (OSM) are well known to those skilled in the art, wherein $Na^+$ variations cause the greatest variations in OSM. The modified Beer-Lambert equation (2) can be utilized to determine osmolarity and $Na^+$. Further, it is also well known by those skilled in the art that variations in OSM or $Na^+$ cause a direct change in the mean cell volume (MCV) of red blood cells (RBCs). When [$Na^+$] increases by 12 millequivalents/liter (meq/L), the microcentrifuge derived hematocrit decreases by one Hematocrit unit (or the MCV decreases by ~2–3%). The proposed method takes advantage of the fact that the log (8)/log (13) ratio is insensitive to [$Na^+$] changes, whereas the log (8) alone, see FIGS. 7, 8 and 9, is very sensitive to $Na^+$ or MCV changes. Log (8) is equal to log ($I/I_o$) at the 810 nm wavelength and log (13) is equal to log ($I/I_o$) at the 1300 nm wavelength.

The actual function of E versus the OSM or $Na^+$ concentration at each given wavelength must hold OSM (or $Na^+$) information that is different in at least one of curvature, offset, linearity, or sign from the other wavelength, see FIG. 7. If the functions of E versus OSM are not sufficiently different, then the ratio $E_1/E_2$ for the two wavelengths will not hold OSM information. FIG. 7. shows the direct affect of Na$^+$ on the optical absorbance (% change in absorbance), for a single wavelength (log (8)) and a dual wavelength device $$\left(\frac{\log(8)}{\log(13)}\right).$$

For a dual wavelength device, the affect of Na$^+$ on the ratio of log (8)/log (13) is minimal. That is, the ratiometric use of two wavelengths cancels competing factors such as Na$^+$.

FIGS. 8 and 9 show that either Na$^+$ or osmolar changes in blood affect the mean cell volume of a red blood cell. In the present invention by measuring one or two appropriate wavelengths a difference will be measured as a function of mean cell value and thus of Na$^+$ or osmolarity. Please note that the lines plotted in FIGS. 8 and 9 should be linear. They are not because the graphs represent actual experimental data measured with the present invention.

Even though wavelengths of 810 nm and 1300 nm are preferred wavelengths, the wavelengths may be selected further apart from one another such that the pathlengthening factors are exaggerated for each wavelength. Therefore, a shorter and longer wavelength are preferred since they exhibit even more sensitivity to scattering. The selection of the measuring wavelength at 585 nm and the reference wavelength at 1550 nm may be more appropriate since the scattering functions (pathlengthening factors) are exaggerated at these two selected wavelengths.

In non-pulsatile applications such as hemodialysis or wherever blood is flowing through a blood chamber or cuvette, then logarithmic operations will give the appropriate computed OSM or Na$^+$ values, see FIGS. 7, 8 and 9, and as shown in the following:

$$[Na^+] = [\log(8)] \cdot F[\log(8)/\log(13)] \quad (15)$$

where F( ) is a function of hematocrit, and $$OSM = g\,[Na^+] + b \quad (16)$$

where OSM is a function of Na$^+$ and g [Na$^+$] is a function of Na$^+$. Further, g is slope and b is offset. Both g and b are empirically determined using known methods that employ a look-up table.

MEASURING PLASMA FREE HEMOGLOBIN

The modified Beer-Lambert equation (2) can also be utilized to determine PFH. In the present invention PFH is determined by using an optical technique that does not distinguish between hemoglobin in red blood cells and hemoglobin in plasma. Rather, when light at 800 nm is shined through blood, each of the elements (red blood cells, plasma and hemoglobin) extinguish a certain amount of light energy as shown by the formula:

$$E_{bulk} = E_{RBC} + E_{plasma} + E_{Hgb\ in\ plasma} + E_{H_2O} + E_{other...} \quad (17)$$

$$= (S_{RBC} + K_{RBC}) + K_p + K_{Hgb\ in\ plasma} + K_{H_2O} + K_{other} \quad (18)$$

where S is a scattering coefficient and K is an absorption coefficient $$= \underbrace{(S_{RBC} + K_{RBC} + K_{Hgb})}_{\substack{membrane\ inside\\ itself\ of\ RBC}} + K_p + K_{Hgb} + K_{H_2O} + K_{other...} \quad (19)$$

Thus: (20)

$$E_{bulk} = \underbrace{(S_{RBC} + K_{RBC} + K_{Hgb})}_{\substack{membrane\ inside\\ itself\ of\ RBC}} +$$

$$(K_{p\ of\ plasma} + K_{Hgb\ in\ plasma}) + K_{H_2O} + K_{other...}$$

From this it can be seen that if there is no hemoglobin in plasma, then $K_{Hgb}=0$. Otherwise, $K_{Hgb}$ adds to the total hemoglobin in plasma and red blood cells.

As an example, at 800 nm wavelength:

$$S_{RBC} = 2.5$$

$$K_{RBC\ membrane} = .05$$

$$K_{Hgb\ inside\ membrane} = .5$$

$$K_{plasma} = .01$$

$$K_{H_2O} = .01$$

$$K_{Hgb\ in\ plasma} = .5$$

$$E_{bulk} = 2.5 + .05 + .5 + .01 + .5 + .01$$
$$= 3.57 \text{ with Hgb in plasma}$$
$$= 3.07 \text{ with no Hgb in plasma}$$

FIG. 10 shows plots of the % change in absorbance of light at 810 nm and 810 nm/1300 nm versus PFH. In this way, FIG. 10 illustrates that using only a single wavelength (800 nm) produces a large % change due to PFH. On the other hand, the ratio of two wavelengths (log (8)/log (13)) nulls out the effects of PFH.

It should be noticed that the following assumptions and requirements are essential in PFH determination.

A. Even though wavelengths of 810 nm and 1300 nm are the preferred wavelengths, the actual function of E versus the PFH concentration at each given wavelength must hold PFH and hematocrit information that is different in curvature, or offset, or linearity, or sign from the other wavelength, see FIG. 10. If the functions of E versus PFH are not sufficiently different, then the ratio E1/E2 for the two wavelengths will not hold PFH information. It will be appreciated that other wavelengths such as 585 nm and 1550 nm would also satisfy the condition of having adequate PFH detected with respect to water.

B. Further, the wavelengths may be selected further apart from one another such that the path-lengthening factors are exaggerated for each wavelength. Therefore, a shorter and longer wavelength are preferred since they exhibit more sensitivity to absorption and scattering. The selection of the measuring wavelength at 585 nm and the reference wavelength at 1900 nm may be more appropriate since the scattering functions (path-lengthening factors) are exaggerated at those two selected wavelengths.

C. FIG. 10 shows that as PFH varies the log (8)/log (13) ratio is unaffected. Whereas, as PFH varies the single wavelength alone, log (8), varies greatly. In other words, the absorption effects due to hemoglobin, whether inside the red blood cell or in the plasma itself, are seen by the detector as a bulk absorbance. When two distinct wavelengths are used, each wavelength will carry, individually, bulk absorbance values. When these two wavelengths are mathematically operated upon ratiometrically the PFH is minimized, see FIG. 10.

D. If monitoring the PFH in living tissue of a patient, the pulsatile characteristics of the blood would require the utilization of the form and mathematical operations as presented in U.S. Pat. No. 5,372,136, using the $\Delta I/I$ technique in order to eliminate certain intrinsic tissue and extrinsic light source effects.

E. In non-pulsatile applications such as hemodialysis or wherever blood is flowing through a disposable conduit, disposable blood chamber, or cuvette; then, logarithmic operations will give the appropriate computed PFH values, see FIG. 10 and as shown in the following:

$$[PFH]=A[log\ (8) \cdot F(log\ (8)/log\ (13))]+B \qquad (21)$$

where A is slope and B is offset. Both A and B are empirically determined using known methods that employ a look-up table.

In this way, it can be appreciated that the present invention is directed toward apparatus and methods for determining the biologic constituent value of the PFH noninvasively. This is achieved by passing at least two wavelengths of light onto or through body tissue such as the finger, earlobe, or scalp or through a disposable extracorporeal conduit for the noninvasive monitoring. Compensating for the effects of competing body tissues and/or the variations in hematocrit is achieved with additional mathematical operations.

The present invention may be embodied in other specific forms without departing from its spirit or essential characteristics. The described embodiments are to be considered in all respects only as illustrative and non-restrictive. The scope of the invention is, therefore, indicated by the appended claims rather than by the foregoing description. All changes which come within the meaning and range of equivalency of the claims are to be embraced within their scope.

What is claimed is:

1. A system for determining a plurality of different constituents of the blood or tissue of a patient, the blood flowing in a pulsatile fashion in a body part of the patient or in an extracorporeal passageway in communication with the circulatory system of the patient so as to be subjectable to transcutaneous examination in the body part or to noninvasive examination in the extracorporeal passageway, the body part or the extracorporeal passageway defining a blood conduit, the system comprising:

blood conduit receiving means for receiving a blood conduit containing the flowing blood of the patient;

a plurality of emitters positioned on said conduit receiving means for emitting a plurality of different radiation wavelengths;

directing means for directing said plurality of radiation wavelengths into the flowing blood in the blood conduit;

detecting means for detecting the amount of radiation for each of said plurality of wavelengths after passing through the blood conduit, said detected amounts of radiation each having different extinction characteristics; and a plurality of determining means each receiving the same one of said plurality of radiation wavelengths from said first detecting means and at least one of said remaining plurality of wavelengths for determining a respective constituent, said plurality of determining means being four and said plurality of constituents being BUN, tissue water content, osmolarity, and Na+.

2. The system of claim 1, wherein said one radiation wavelength is 1300 nm.

3. The system of claim 1, wherein said blood and tissue constituents are selected from the group consisting of BUN, PFH, tissue water content, hematocrit, hemoglobin, osmolarity, and $Na^+$.

4. The method of claim 1, wherein said first radiation wavelength is 2190 nm.

5. The method of claim 1, wherein said first radiation wavelength is 810 nm.

6. A method for determining BUN of a patient, the blood flowing in a pulsatile fashion in a body part of the patient or in an extracorporeal passageway in communication with the circulatory system of the patient so as to be subjectable to examination in the extracorporeal passageway, in the body part or the extracorporeal passageway defining a blood conduit, the method comprising the steps of:

flowing the blood of a patient through a blood conduit;

placing a first emitter emitting a first radiation wavelength on the blood conduit; directing the first radiation wavelength through the blood on the blood conduit;

detecting the amount of first radiation after passing through the blood in the blood conduit, the detected amount of first radiation having at least one extinction characteristic; and determining a plurality of blood constituents based on the detected amount of first radiation in accordance with the equation $I=I_o e^{[-E(x)d+B(d,\ E(x))]}$, where B(d, Ex) is an optical pathlengthening function, $I_o$ is the intensity of the incident source radiation, I is the transmitted intensity of the source radiation through the sample, E is the extinction coefficient of the sought for constituent, x is the concentration of the BUN and d is the optical separation distance.

7. The method of claim 5, wherein the one radiation wavelength is 1300 nm.

8. A system for determining BUN of a patient, the blood flowing in a pulsatile fashion in a body part of the patient or in an extracorporeal passageway in communication with the circulatory system of the patient so as to be subjectable to transcutaneous examination in the body part or to noninvasive examination in the extracorporeal passageway, the body part or the extracorporeal passageway defining a blood conduit, the system comprising:

blood conduit receiving means for receiving a blood conduit containing the flowing blood of the patient;

a first emitter positioned on said conduit receiving means for emitting a first radiation wavelength;

directing means for directing the first radiation wavelength into the flowing blood in the blood conduit;

first detecting means for detecting the amount of first radiation after passing through the blood conduit, said detected amount of first radiation having at least one extinction characteristic; and determining means receiving said first radiation from said first detecting means for determining BUN by solving the equation $\log\ [I/I_o)_{2190}/(I/I_{o1300}] \cdot [F[\log\ (I/I_o)_8/\log\ (I/I_o)_{13}]]$, where $E_{2190}$ equals the extinction coefficent at 2190 nm wavelength, $E_{1300}$ equals the extinction coefficient at 1300 nm wavelength, F equals a function of hematocrit, I equals the transmittal intensity of source radiation, $I_o$ equals the intensity of incident source radiation; $\log\ (I/I_o)_8$ is the log value at 810 nm wavelength and $\log\ (I/I_o)_{13}$ is the log value at 1300 nm wavelength.

* * * * *

UNITED STATES PATENT AND TRADEMARK OFFICE
CERTIFICATE OF CORRECTION

PATENT NO. : 6,246,894 B1  Page 1 of 1
DATED : June 12, 2001
INVENTOR(S) : Robert R. Steuer et al.

It is certified that error appears in the above-identified patent and that said Letters Patent is hereby corrected as shown below:

<u>Title page,</u>
Item [63], Related U.S. Application Data, after "136," delete "which is a continuation of application No. 08/598,169, filed on Feb. 7, 1996, now Pat. No. 5,734,502,".

Signed and Sealed this

Thirteenth Day of April, 2004

JON W. DUDAS
*Acting Director of the United States Patent and Trademark Office*